(12) United States Patent
Czech et al.

(10) Patent No.: US 6,174,983 B1
(45) Date of Patent: Jan. 16, 2001

(54) SILICONE TERPOLYMERS WITH HIGH REFRACTIVE INDICES

(75) Inventors: Anna Czech, Cortlandt Manor; Jeffrey A. Cooke, Brewster, both of NY (US)

(73) Assignee: C. K. Witco Corporation, Greenwich, CT (US)

( * ) Notice: Under 35 U.S.C. 154(b), the term of this patent shall be extended for 0 days.

(21) Appl. No.: 09/190,534

(22) Filed: Nov. 12, 1998

Related U.S. Application Data

(60) Provisional application No. 60/065,211, filed on Nov. 12, 1997.

(51) Int. Cl.$^7$ .......................... C08G 77/04; C08G 77/42; C08G 77/445; C08G 77/46
(52) U.S. Cl. .................. 528/25; 528/15; 528/16; 524/267; 524/366
(58) Field of Search ................. 528/15, 16, 25; 524/267, 366

(56) References Cited

U.S. PATENT DOCUMENTS

| | | | |
|---|---|---|---|
| 3,233,986 | 2/1966 | Morehouse . | |
| 3,299,112 | 1/1967 | Bailey . | |
| 3,389,159 | 6/1968 | Nielsen . | |
| 3,507,815 | 4/1970 | Bailey et al. . | |
| 3,935,133 | 1/1976 | Van Leuwen et al. | 260/2.5 |
| 4,746,683 | 5/1988 | Kilgour | 521/112 |
| 4,854,938 | 8/1989 | Easton et al. | 44/56 |
| 4,996,277 | 2/1991 | Bradshaw et al. | 528/15 |
| 5,041,468 | 8/1991 | Budnik et al. | 521/112 |
| 5,045,571 | 9/1991 | Blevins et al. | 521/112 |
| 5,070,112 | 12/1991 | Grabowski | 521/112 |
| 5,145,879 | 9/1992 | Budnik et al. | 521/112 |
| 5,192,812 | 3/1993 | Farris et al. | 521/112 |
| 5,231,157 | 7/1993 | Herzig et al. | 528/15 |
| 5,424,384 | 6/1995 | Gentle et al. | 528/34 |
| 5,432,206 | 7/1995 | Stanga et al. | 521/110 |
| 5,446,119 | 8/1995 | Herzig et al. | 528/26 |
| 5,474,709 | 12/1995 | Herzig et al. | 252/321 |
| 5,489,617 | 2/1996 | Miller et al. | 521/112 |
| 5,492,939 | 2/1996 | Stanga et al. | 521/112 |
| 5,542,960 | 8/1996 | Grabowski | 44/320 |
| 5,620,485 | 4/1997 | Fey | 44/320 |
| 5,650,449 | 7/1997 | Mukuno et al. | 521/111 |
| 5,773,484 | 6/1998 | Miller | 521/174 |
| 5,789,454 | 8/1998 | McVey | 521/112 |
| 5,844,010 | 12/1998 | Burkhart et al. | 521/112 |

FOREIGN PATENT DOCUMENTS

| | | |
|---|---|---|
| 56102 | 3/1969 | (DE) . |
| 0662334A2 | 3/1994 | (EP) . |
| 707906 | 6/1950 | (GB) . |
| 94/08557 | 4/1994 | (WO) . |

OTHER PUBLICATIONS

Organofunctionalized Silicone Resins For Personal Care Applications, M.D. Berthiaume and A.D. Baum, J. Soc. Cosmet Chem. Jan./Feb. 1997.

*Primary Examiner*—Robert Dawson
*Assistant Examiner*—Jeffrey B. Robertson
(74) *Attorney, Agent, or Firm*—Shirley S. Ma, Esq.

(57) ABSTRACT

Silicone terpolymers, modified with phenyl or substituted phenyl groups and polyalkyleneoxides, which exhibit refractive indices >1.47 are disclosed. These materials of the present invention when incorporated in formulations for surface treatment improve slip and gloss of the substrates to which they are applied, and are useful in hair care and coatings applications.

10 Claims, 2 Drawing Sheets

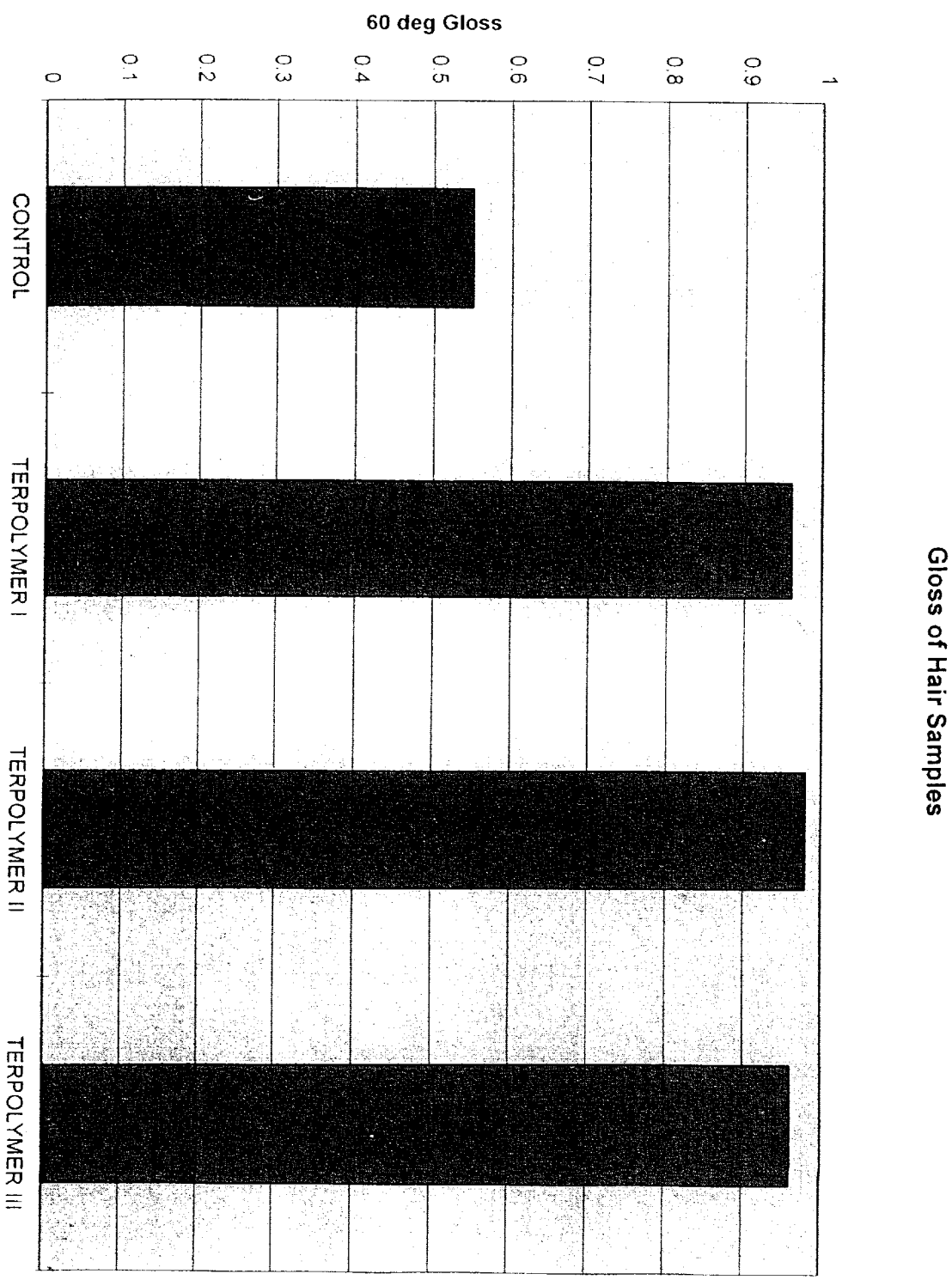

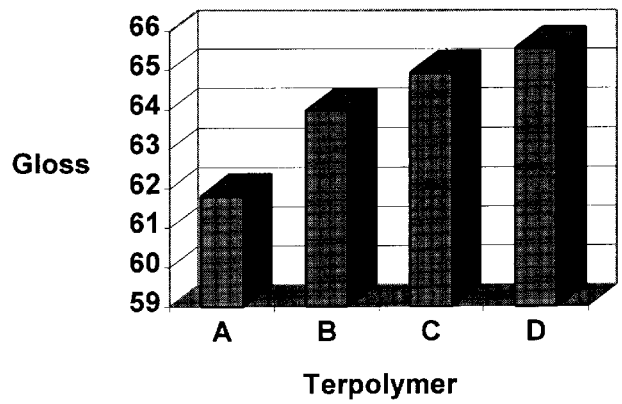
Figure 2: Gloss of Terpolymers in UV cured acrylate formulation
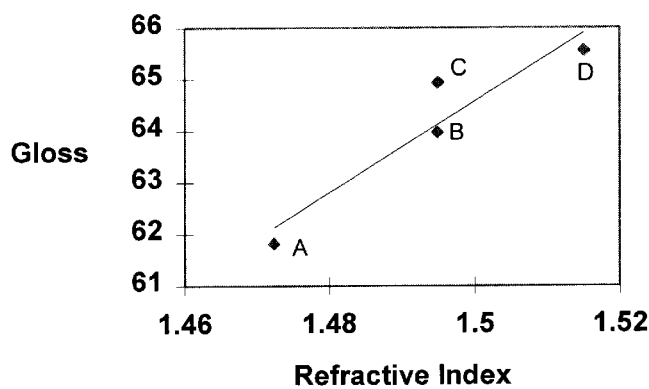
Figure 3: Correlation between refractive index of terpolymer and gloss of cured formulation.

SILICONE TERPOLYMERS WITH HIGH REFRACTIVE INDICES

This application claims priority from copending provisional application No. 60/065,211 filed Nov. 12, 1997.

FIELD OF THE INVENTION

The present invention concerns substituted polysiloxanes having high refractive indices.

BACKGROUND

Phenyl and phenethyl groups pendant polysiloxanes with high refractive indices are useful in applications that benefit from improved surface slickness and gloss, such as hair care and coatings. See, e.g., U.S. Pat. No. 3,389,159 and German Patent 56,102 which provide synthesis of polysiloxanes with phenyl substitution. A review article by M. Berthiaume et al., *J. Soc. Cosmetic Chemists*, No.1, 1997, provides performance data of the phenyl-substituted and phenethyl-substituted silicones on hair.

WO 94/08557 provides examples of the hair care compositions providing conditioning and enhanced shine to the hair comprising the combination of high refractive index, non-volatile aryl substituted polysiloxanes, a novolatile spreading agent which is compatible with the polysiloxane fluid and a carrier suitable for hair care application. However, generally, phenyl substituted polysiloxanes are not readily compatible with personal care matrices.

U.S. Pat. No. 5,542,960 teach a class of silicone polymers modified with both phenol derivatives substituents such as eugenol, and polyether grafted onto a silicone backbone for diesel antifoam applications. Such polysiloxanes tend to have viscosities which are too high for use in personal care formulations though.

BRIEF DESCRIPTION OF THE DRAWINGS

FIG. 1 is the Gloss of Hair Samples according to the examples.

FIG. 2 is the Gloss of Terpolymers in UV cured acrylate formulations.

FIG. 3 is a correlation between the gloss and the refractive index of the terpolymer used.

SUMMARY OF THE INVENTION

The present invention relates to fluids comprising terpolymers of (a) aryl component including phenyl or substituted phenyl groups with at least one hydrocarbon side chain of 2–5 carbons; (b) polyalkyleneoxide, and (c) silicone. Most preferably these terpolymers have refractive indices (RI) >1.47. Fluids of the present invention when incorporated in compositions employed as surface treatments improve slip and gloss of the substrates to which the compositions are applied. They also offer an advantage over phenyl-substituted and phenethyl-substituted materials in compatibility with media commonly used in hair care applications.

DETAILED DESCRIPTION OF THE INVENTION

The present invention is directed more specifically to polysiloxanes of the general formula (I)

wherein:

Q is R, $R^1$ or $R^2$; but at least one Q is $R^1$ and at least one Q is $R^2$.

R is a monovalent saturated straight, branched, or cyclic alkyl group having 1 to 10 carbon atoms. Each of the R groups present may be the same or different from one another. Examples of R groups include methyl, ethyl, butyl, hexyl. Of these, lower alkyl groups ($C_1$–$C_4$) are preferred. Most preferably R is methyl.

$R^1$ is —$R^3$—$C_6H_3R^4R^5$ where $R^3$ is a divalent hydrocarbon group of 2–5 carbons, $R^4$ and $R^5$ are the same or different and selected from hydrogen, a $C_1$–$C_6$ alkyl, a $C_1$–$C_6$ alkoxy group, a tri-($C_1$–$C_6$-alkyl)siloxy group, or an acyloxy group $R^AC(O)O$— (wherein $R^A$ is $C_1$–$C_{10}$ alkyl, aryl (preferably phenyl), or an aryl-$C_1$–$C_{10}$-alkyl (such as benzyl or phenethyl)), an amide, (—$OC_vH_{2v}$)$_l$$OR^7$ (wherein v is 2 to 4, l is 1 to 10 and $R^7$ is hydrogen or R above); preferably $R^4$ and $R^5$ are in the para and meta positions on the phenyl ring; alkoxy groups are the most preferred. Preferably at least one of $R^4$ and $R^5$ are not hydrogen; most preferably one is an alkoxy group. Specific $R^3$ may be —$C_3H_6$; and —$C_4H_8$—.

$R^2$ is represented by formula —$(C_mH_{2m})(OC_nH_{2n})_pOR^6$ (II), where $R^6$ can be hydrogen, R, or acetyl. "m" is an integer greater than 0, each n is 2 to 4, p is from 0 to 100. Preferably, "m" ranges from 2 to 8, and n is 2 or 3, most preferably 2. Mixtures of different values of n are possible within one $R^2$ group.

Generally d is 0 to 4, e is 0 to 4, g is 0 to (2*d+e+2) and f is 1 to 500. In linear siloxanes, d is 0, e is 0, g is 2 and f is from 1 to 500. In cyclic siloxanes, d is 0, e is 0, g is 0 and f is from 4 to 12. In branched siloxanes, d is 0 to 4, e is 0 to 4, g is 2*d+e+2; and f is 1 to 500. Preferably f is from 5 to 100, most preferably 10 to 50.

The actual siloxane chain length does not affect substantially the refractive index; rather it is the ratio of the number of $R^1$ to R and $R^1$ to $R^2$, with $R^1$ increasing RI and each R and $R^2$ decreasing the RI. The ratio of the number $R^1$ to R+$R^2$ is 1:5 to 20:1, more preferably 1:2 to 10:1. As stated it is preferred to modify this ratio to achieve an RI>1.47 so that the polysiloxane will have an appropriate gloss level.

Unlike terpolymers defined by U.S. Pat. No. 5,334,227, terpolymers of the present invention do not contain phenolic functionality; presence of free hydroxyl groups on aromatic substituents resulted in high viscosity copolymers with less desirable tactile properties.

The index of refraction is the ratio of the speed of light in a vacuum to the speed of light in the medium. This is a dimensionless parameter which ranges between 1.3 and 1.55 for most of organic liquids. The refractive index is measured using a beam of monochromatic light, typically, the yellow light of the sodium D line (wavelength λ=589.3 nm). Thus $n^{25}_D$ indicates the wavelength used D, and the temperature 25° C. Other wavelengths used are C and F line of hydrogen and G line of mercury, but for purposes of the present invention references are to the D line.

Manufacture

Terpolymers of the present invention can be prepared by platinum catalyzed hydrosilation reaction of an allyl started phenyl derivative (e.g., of formula $CH_2$=$CHCH_2C_6H_3$ ($OCH_3$)($OR_3$)) and the terminally unsaturated polyalkyleneoxide (of formula $CH_2$=$CH$—$(C_{m-2}H_{2m-4})(OC_nH_{2n})_pOR^6$ with hydrogen-substituted silanic fluid under typical hydrosilation conditions, such as those disclosed in U.S. Pat. Nos. 3,299,112 and 5,334,227, which are incorporated herein by reference.

According to the *Comprehensive Handbook on Hydrosilation*, edited by Bogdan Marciniec (Pergamon Press, First Edition 1992) (incorporated by reference herein), hydrosilation is a term that describes addition reaction of silicon hydrides to the multiple bonds such as carbon—carbon, carbon—oxygen, carbon—nitrogen and nitrogen—oxygen. The reaction can proceed according to a free-radical mechanism. Alternatively, when catalyzed by transition metal salts and complexes as well as other catalysts the mechanism may be predominantly polar. The catalyst can be selected from the group of platinum, palladium, rhodium and ruthenium, less commonly nickel or aluminum in the form suitable for either homo- or heterogenous catalysis. Most commonly hydrosilation reactions are catalyzed by platinum catalyst such as chloroplatinic acid.

Eugenol and some of its ethers and esters of the foregoing formula (I) are commercially available. Eugenol ethers and esters of formula (I) can be prepared according to known procedures suitable for preparation of aromatic ethers (e.g., C. Moreau, F. Roessac, J. M. Conia, *Tetrahedron Lett.*, 3527, 1970; H. N. Grant, V. Prelog, R. P. A. Sneeden, *Helv. Chim. Acta*, 46, 415, 1963) and of aromatic esters (e.g., V. O. Illi, *Tetrahedron Lett.*, 2431, 1979; P. A. Stadler, *Helv. Chim. Acta*, 61, 1675, 1978), which are incorporated herein by reference.

Use

The terpolymers of the present invention can be used neat, or for ease of application they can be applied dissolved, dispersed or emulsified in a suitable liquid medium, such as water, alcohol, glycols, other silicones, etc. Particular silicones which may be used are cyclic siloxanes and low viscosity oils (<100 cps).

Standard surfactants may be used in such liquids, such as anionic, nonionic and cationic surfactants. Particular classes of surfactant would be polyether modified polysiloxanes and polysorbates.

Other additives typically employed in hair care applications can be included with the terpolymers of the present invention or applied separately to the substrate. Such additives can include resins, preservatives, biocides, biostats, pigments, dyes, fragrances, pH buffers, antifoams and defoamers.

Personal care applications, especially those where clarity may be an issue may be made with terpolymers of the present invention, including, but not limited to, nail polishes, anti-perspirants, body washes, mascara, soaps, detergents, etc. Examples of the hair care formulations that can benefit from the incorporation of the terpolymers of the present invention include shampoos, rinse conditioners, hair dressings, leave-in conditioners, styling mousses and hair sprays. See, e.g., WO 94/08857, which is incorporated herein by reference.

Moreover, terpolymers of the present invention may be used in other applications, most preferably coating compositons, such as car care, decorative coatings and overprint varnishes wherein the gloss of the final product is important.

EXAMPLES

The following specific examples are set forth for illustration only and are not to be construed as limiting of the present invention. For the examples M is $(Me)_3SiO_{1/2}$; D is $[O_{1/2}Me_2SiO_{1/2}]$; D* is $[O_{1/2}MeSiR^1O_{1/2}]$; and D' is $[O_{1/2}MeSiR^2O_{1/2}]$. The instrument used to determine refractive indices of the polysiloxanes of the present invention was LEICA ABBE MARK II Refractometer, utilizing line D light at 25° C.

Example 1

Hair evaluations were performed on 10 inch (25.4 cm) tresses of Oriental hair. Hair tresses were soaked in toluene for 10 minutes to remove any natural oils that could contribute to the gloss. Terpolymers I–III (Table 1) were dissolved in isopropanol to a concentration of 0.1 wt. %, and 1 cc of each solution was applied and worked through the tresses; control tresses were treated with isopropanol. All tresses were then air dried for 1 hour. Hair evaluations were performed by a panel of three observers who compared gloss and feel of the treated samples to the untreated control. The results are summarized in Table 2.

TABLE 1

Structural Information

| | Formula | Refractive Index | Viscosity (cps) - 25° C. |
|---|---|---|---|
| Terpolymer I (control derived from eugenol) | $MD_5D^*_6D''_1M$ wherein $R^1$ is $—C_3H_6—C_6H_3(OH)(OCH_3)$ wherein $R^2$ is $—(CH_2)_3(OC_2H_4)_bOCH_3$, with b a number such that $R^2$ has an average MW = 350 | 1.50 | 3700 |
| Terpolymer II | $MD_5D^*_6D''_1M$ wherein $R^1$ $—C_3H_6—C_6H_3(OCH_3)_2$ $R^2$ is $—(CH_2)_3(OC_2H_4)_bOCH_3$ with $R^2$ of average MW = 350 | 1.49 | 880 |
| Terpolymer III | $MD_5D^*_{6.5}D''_{0.5}M$ wherein $R^1$ $—C_3H_6—C_6H_3(OCH_3)_2$ $R^2$ is $(CH_2)_3(OC_2H_4)_bOCH_3$ with $R^2$ of average MW = 350 | 1.51 | 942 |

TABLE 2

Hair Testing Results

| Hair Sample | Gloss Compared to Control | After-Feel Compared to Control |
|---|---|---|
| Terpolymer I | improved | softer, tacky |
| Terpolymer II | improved | smoother, softer |
| Terpolymer III | improved | smoother, softer |

All terpolymers imparted gloss to hair. The terpolymer structures that had been modified with eugenol ether offered better after-feel. In addition, gloss of these hair tresses has been assessed using the following non-subjective test method:

60° Gloss—Gloss data were generated using a Micro-Tri-Gloss Portable GlossMeter (Byk-Garnder). Two tresses were prepared and measured for each finish. Each tress was subjected to eight readings taken at 45° increments by rotating the meter on the hair tress. An average of the eight readings was calculated for each hair tress. A data point was generated from the average of two tresses for each finish. The data is presented in FIG. 1. Gloss values of hair samples treated with high refractive index copolymers were higher than the untreated control.

Example 2

The 20° gloss of Terpolymers A–D (as given in Table 3) was evaluated in the following model acrylate UV cured overprint varnish formulation:

| Component | Manuf. | pph |
|---|---|---|
| EBECRYL 745 | UCB Radcure | 35 |
| Trimethylolpropane triacrylate | Aldrich Chem. Co. | 47 |
| Tripropylene glycol diacrylate | Aldrich Chem. Co. | 10 |
| IRGACURE 184 | Ciba Specialty Chem. Co. | 7 |
| Terpolymer | | 1 |

The formulations were drawn down on Leneta unlacquered opacity charts using a TMI K-Control coater equipped with a #3 wire wound rod (5 panels per group for a total of 20 panels). The drawdowns were completed at #4 speed, and the panels cured at 300 mJ/cm$^2$ using a bench top UV curing unit (UV Process Supply Inc.). The 20° gloss of the cured panels was measured one hour after curing using a Mini Tri-Gloss Portable Glossmeter (Byk-Gardner Inc.).

TABLE 3

Structural Information for Terpolymers A, B, C, D.

| | Formula | Refractive Index |
|---|---|---|
| Terpolymer A | $MD_5D^*{}_3D''{}_4M$ wherein $R^1$ is —$C_3H_6$—$C_6H_3(OCH_3)_2$ $R^2$ is $(CH_2)_3(OC_2H_4)_bOCH_3$ with $R^2$ of average MW = 350 | 1.4723 |
| Terpolymer B | $MD_5D^*{}_5D''{}_1M$ wherein $R^1$ —$C_3H_6$—$C_6H_3(OCH_3)_2$ $R^2$ is $(CH_2)_3(OC_2H_4)_bOCH_3$ with $R^2$ of average MW = 350 | 1.4949 |
| Terpolymer C | $MD_5D^*{}_6D''{}_1M$ wherein $R^1$ —$C_3H_6$—$C_6H_3(OCH_3)_2$ $R^2$ is $(CH_2)_3(OC_2H_4)_bOCH_3$ with $R^2$ of average MW = 350 | 1.4950 |
| Terpolymer D | $MD_5D^*{}_{6.5}D''{}_{0.5}M$ wherein $R^1$ is —$C_3H_6$—$C_6H_3(OCH_3)_2$ wherein $R^2$ is $(CH_2)_3(OC_2H_4)_bOCH_3$ with $R^2$ of average MW = 350 | 1.5150 |

The results are summarized in FIGS. 2 and 3. FIG. 2 shows the 20° gloss measurements of the four terpolymers, while FIG. 3 shows the correlation between the gloss of the formulation and the refractive index of the terpolymer. Clearly as the refractive index of the cured terpolymer increases, the measured gloss of the cured formulation increases.

Example 3
Evaluation of Gloss Enhancement in Tire Dressing

"Son of a Gun", a commercially available tire dressing formulation, as received and containing 0.2% of the Terpolymer II were applied onto SBR (styrene-butadiene rubber) sheets rinsed with water to remove excess dust. 0.2 g of the formulation was applied in 3–4 draw-downs with the manual draw-down machine, #3 wire wound rod. The 60° gloss of the air dried samples was measured using a glossmeter as above. Results are summarized in Table 4.

TABLE 4

Gloss Measurements of the Rubber Samples

| | Gloss Values | | | | Average |
|---|---|---|---|---|---|
| "Son of a Gun" Blank | 18.8 | 35.5 | 42 | 40.7 | 34 |
| | 19.9 | 35.3 | 43.2 | 38.6 | |
| "Son of A Gun/" Terpolymer III | 62.9 | 71.3 | 67.5 | 37.3 | 60.5 |
| | 63.3 | 70.4 | 65.7 | 44.6 | |

Incorporation of the Terpolymer II into the tire dressing formulation enhanced the gloss of the treated rubber.

Example 4
Formulations

The following are examples of the model hair care formulations featuring polysiloxanes of the present invention:

Gloss Enhancing Clear Shampoo
Formula:

| Ingredients | Wt Percent |
|---|---|
| WITCOLATE NH (Witco Corp.) (Ammonium Lauryl Sulfate, 28%) | 35.7 |
| WITCAMIDE CMEA (Witco Corp.) (Cocamide MEA) | 2.2 |
| PEG-120 Methyl Glucose Dioleate, | 2.0 |
| Terpolymer III | 0.3 |
| Citric Acid, anhydrous | 0.4 |
| REWOTERIC AMB14 (Witco Corp.) (Coacamidopropyl Betaine, 35%) | 10.0 |
| Deionized Water | qs |
| Preservative | qs |

Mixing Instructions: With propeller agitation, mix deionized water and ammonium lauryl sulfate. Heat to 45° C. and add remaining ingredients in the order listed, waiting for each ingredient to dissolve before adding the next. Cool to room temperature. At the recommended use level, Terpolymer III may cause slight haze and up to 20% viscosity decrease depending on the primary surfactants system. Clarity of the shampoo may be improved by pre-blending Terpolymer III with dipropylene glycol at 1:5 ratio.

Gloss Enhancing Hair Conditioner
Formula:

| Ingredients | Wt Percent |
|---|---|
| Terpolymer III | 0.30 |
| VARISOFT CRC (Witco Corp.) (quatemulsifier) | 5.00 |
| "ACTISEA" TM 100 (Active Organics, Inc.) (seaweed extract) | 0.50 |
| DL "PANTHENOL" (Tri-K Industries, Inc.) (provitamin B) | 0.20 |
| Citric Acid | 0.05 |
| Deionized Water | qs |
| Preservative | qs |

Mixing Instructions: While agitating the water, add citric acid and Varisoft® CRC. With mixing, heat to 75–80° C. and add remaining ingredients. Cool to room temperature with mixing. Adjust to pH 4.5–5.5 with citric acid if necessary. Add preservative as needed.

Low VOC Pump Hair Spray with Enhanced Gloss
Formula:

| Ingredients | Wt Percent |
|---|---|
| BALANCE ™, 50% Resin - National Starch (polyacrylate) | 8.0 |
| Terpolymer III | 0.1 |
| Ethanol, denatured | 55.0 |
| Aminomethyl Propanol (MPA) to pH 7 | qs |
| Deionized Water | qs |

Mixing Instructions: Combine Balance Resin, water ethanol and Terpolymer III. While agitating, add MPA.

Clear Styling Gel with Enhanced Gloss
Formula:

| Ingredients | Wt Percent |
|---|---|
| Phase A | |
| Deionized Water | 67.0 |
| Carbomer 940 -BF Goodrich - polyacrylic acid | 0.8 |
| Phase B | |
| Triethanolamine | 0.8 |
| Phase C | |
| Kemester USP (Witco Corp.) (Glycerin) | 3.0 |
| Propylene Glycol | 3.0 |
| Phase D | |
| Deionized Water | 22.3 |
| PVP (PVP-K30) (ISP) (polyvinyl pyrrolidone) | 2.0 |
| Phase E | |
| Terpolymer III | 0.1 |
| TWEEN 20 (ICI) (polysorbate) | 1.0 |

Mixing Instructions: Combine ingredients of Phase A, add Phase B with mixing. Add phase C. Premix ingredients of Phase D and add to the batch while mixing. Add premixed components of Phase E and mix until uniform.

What is claimed is:

1. Polysiloxanes of the general formula (I)

$$[SiO_{4/2}]_d[MeSiO_{3/2}]_e[O_{1/2}MeSi(Q)O_{1/2}]_f[O_{1/2}Me_2SiQ]_g \quad (I)$$

wherein:
- Q is R, $R^1$ or $R^2$; but at least one Q is $R^1$ and at least one Q is $R^2$;
- R is a monovalent saturated straight, branched, or cyclic alkyl group having 1 to 10 carbon atoms, wherein each of the R groups present may be the same or different from one another;
- $R^1$ is —$R^3$—$C_6H_3R^4R^5$ where
  - $R^3$ is a divalent hydrocarbon group of 2–5 carbons,
  - $R^4$ and $R^5$ are the same or different and selected from the group consisting of hydrogen; a $C_1$–$C_6$ alkyl; a $C_1$–$C_6$ alkoxy group; a tri-($C_1$–$C_6$-alkyl)siloxy group; an acyloxy group $R^A C(O)O$—, wherein $R^A$ is $C_1$–$C_{10}$ alkyl, aryl, or an aryl-$C_1$–$C_{10}$-alkyl; an amide; and —$(OC_vH2_v)_lOR^7$, wherein v is 2 to 4, l is 1 to 10 and $R^7$ is hydrogen or a group as defined for R, and
  - at least one of $R^4$ and $R^5$ is not hydrogen;
- $R^2$ is represented by formula —$(C_mH_{2m})(OC_nH_{2n})_pOR^6$, where $R^6$ is hydrogen, R or acetyl; m is an integer greater than zero; each n is 2 to 4; p is from 0 to 100;
- d is 0 to 4, e is 0 to 4, g is 0 to (2d+e+2) and f is 1 to 500.

2. A polysiloxane according to claim 1 comprising at least one said R-group and wherein R is methyl.

3. A polysiloxane according to claim 2 wherein $R^4$ and $R^5$ are in the para and meta positions on the phenyl ring.

4. A polysiloxane according to claim 3 wherein at least one of $R^4$ and $R^5$ are alkoxy groups.

5. A polysiloxane according to claim 2 wherein d is 0, e is 0, g is 2 and f is from 1 to 500.

6. A polysiloxane according to claim 4 wherein d is 0, e is 0, g is 0 and f is from 4 to 12.

7. A polysiloxane according to claim 2 which has a refractive index >1.47.

8. A composition comprising a polysiloxane according to claim 1 and an emulsifier.

9. A coating composition incorporating the polysiloxane of claim 2.

10. A hair care formulation incorporating the polysiloxane of claim 2.

* * * * *